Figure 1:
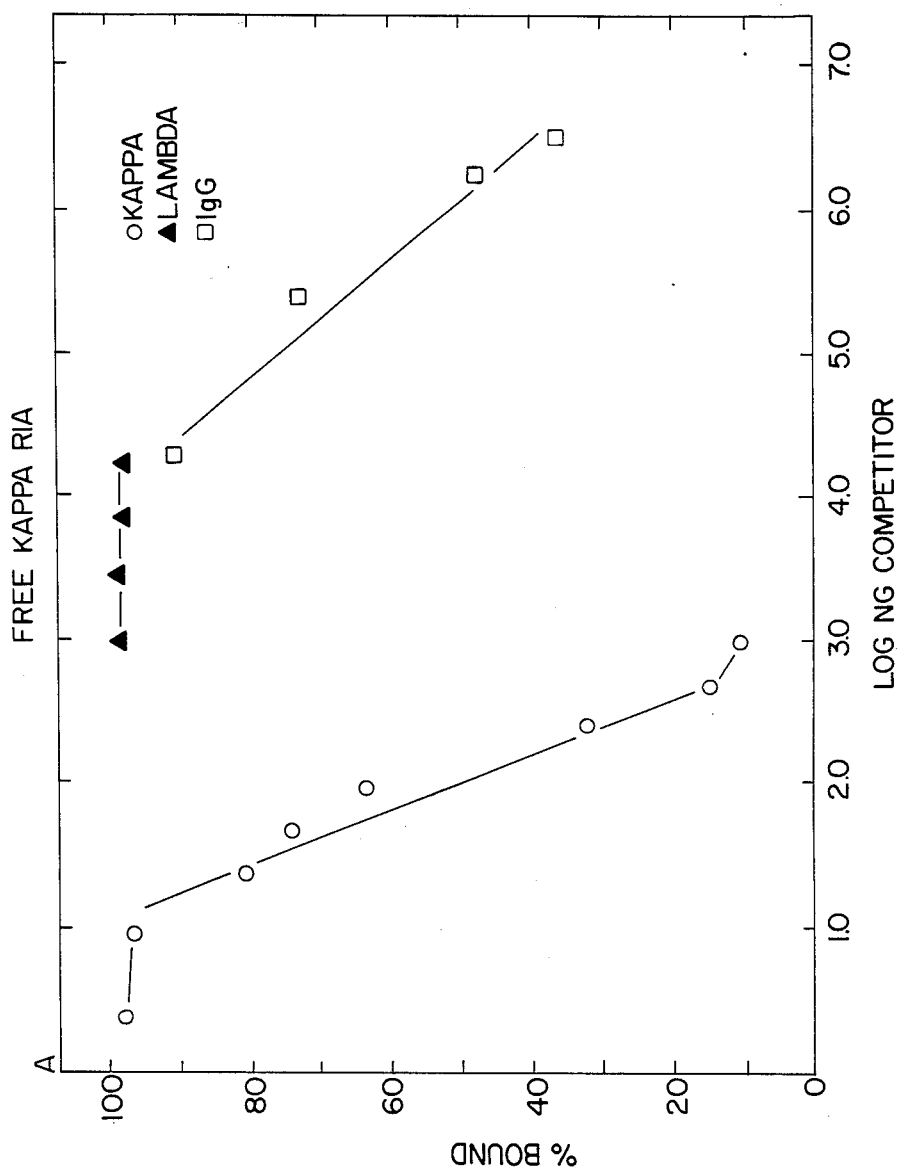

United States Patent [19]

Rudick et al.

[11] Patent Number: 4,792,529
[45] Date of Patent: Dec. 20, 1988

[54] IMMUNOASSAY OF FREE KAPPA LIGHT CHAINS FOR THE DETECTION OF MULTIPLE SCLEROSIS

[75] Inventors: Richard A. Rudick; Robert M. Herndon; Jean M. Bidlack, all of Rochester, N.Y.

[73] Assignee: University of Rochester, Rochester, N.Y.

[21] Appl. No.: 789,269

[22] Filed: Oct. 18, 1985

[51] Int. Cl.$^4$ .................. G01N 33/534; G01N 33/53; G01N 33/68
[52] U.S. Cl. .................................... 436/542; 436/545; 436/811
[58] Field of Search ............... 436/539, 542, 545, 811; 435/7

[56] References Cited

U.S. PATENT DOCUMENTS

| | | | |
|---|---|---|---|
| 4,136,160 | 1/1979 | Cohen | 424/1 |
| 4,205,057 | 5/1980 | Whitaker | 436/540 |
| 4,294,818 | 10/1981 | McMichael et al. | 436/547 |

OTHER PUBLICATIONS

Lechky, O., Medical Tribune, vol. 26, No. 19, Jul. 3, 1985, p. 11.
Lechky, O., The Medical Post, vol. 21, No. 10, May 14, 1985.
Shaw, P., Inside MS, vol. 3, No. 3, Summer 1985, p. 14.
Research, Annual Report of National MS Society, Diagnostic Aid, 1985, p. 5.
Matteson et al., Light Chain Composition of CSF . . . , J. Neuro Imm. 3:63 (1982).
Link et al., Immunoglobulin Class and Light Chain Type of Oligoclonal . . . , Ann. Neurology 2:107 (1979).
Link et al., Multiple Sclerosis: Disturbed Kappa: Lambda Chain Ratio . . . , Clin. Exp. Imm. 6:435 (1970).
Vandvik, R., Oligoclonal IgG and Free Light Chains in the Cerebral . . . , Scand. J. Imm. 6:913 (1977).
Laurenzi et al., Oligoclonal IgG and Free Light Chains in Multiple Sclerosis . . . , Ann. Neurology 8:241 (1980).
Rudick et al., Free Light Chains in the CSF of Patients with . . . , Neurology 35:271 (1985).
Poser et al., New Diagnostic Criteria for Multiple Sclerosis . . . , Ann. Neurology 13:227 (1983).
Perini et al., Evidence for Heterogeneous or Incomplete Immunoglobulins . . . , Clinica Chimica Abst. 96:205 (1979).
Riberi et al., Evidence for the Presence of λ Chain Dimers in Cerebrospinal . . . , Clin. Exp. Imm. 19:45 (1975).
Solling, K., Free Light Chains of Immunoglobulins in Normal Serum and Urine . . . , Scand. J. Clin. Lab. Invest. 35:407 (1975).

Primary Examiner—David M. Naff
Attorney, Agent, or Firm—Martin LuKacher

[57] ABSTRACT

Multiple sclerosis (MS) is diagnosed by determining with a quantitative immunoassay the quantity of free kappa light chains in the cerebrospinal fluid of a patient. The immunoassay is preferably a radioimmunoassay. In carrying out the immunoassay, the free kappa light chains are combined with antiserum specific thereto. This method of diagnosing MS has high sensitivity in distinguishing between normal patients and patients affected with MS.

7 Claims, 2 Drawing Sheets

IMMUNOASSAY OF FREE KAPPA LIGHT CHAINS FOR THE DETECTION OF MULTIPLE SCLEROSIS

This invention relates to the field of diagnostic radioimmunoassays. More particularly, the invention relates to the detection of multiple sclerosis (MS) by quantifying the presence of free kappa light chains in a patient's cerebral spinal fluid (CSF).

MS is a degenerative condition affecting the myelin component of central nervous tissue. Patients with MS exhibit abnormalities of immunoglobulin G (IgG). Largely restricted to the central nervous system (CNS), these abnormalities include increased amounts of IgG in brain and CSF; restricted electrophoresis, subclass, and allotype characteristics of IgG; immune complexes in CSF; and an increased CSF kappa:lambda light chain ratio. The specificities of most of the IgG antibodies and the nature of their involvement in myelin injury, however, are unknown.

Various lines of evidence have shown that IgG is increased in CSF selectively relative to other proteins. This may be due to synthesis of antibodies within the nervous system. A selective increase in CSF IgG has been observed so consistently in MS that the increase in IgG has become the best known laboratory test for confirmation of the diagnosis. The finding is nonspecific, however, in that a substantial proportion of control patients with CNS infections or inflammatory diseases also have elevated CSF IgG.

Similarly, free kappa and lambda light chains also have been reported in patients with MS. Light chains (either kappa or lambda, but not both) are components of all classes of immunoglobulins, wherein they combine with the heavy chains to form a specific immunoglobulin. Light chains also may exist in a free state (i.e., not bound to a heavy chain) in patients with various forms of myeloma tumors. These free light chains are commonly known as Bence-Jones proteins. The kappa and lambda light chains form individual Bence-Jones proteins which differ in their amino acid sequence.

The presence of free light chains in patients with MS has prompted several investigators to use polyacrylamide gel isoelectric focusing to isolate free kappa light chains in CSF. See, e.g., Link, et al., *Immunoglobulin Class and Light Chain Type of Oligoclonal Bands in CSF* . . . , Ann. Neurol., 6:107 (1979). Detection of these chains typically followed immunofixation with an antibody directed to the free kappa light chains. This technique, however, provides only for a qualitative determination of the free kappa light chains rather than provide for a quantitative determination.

Alternatively, a radioimmunoassay has been disclosed in an attempt to describe the light chain composition of CSF in patients with MS. See Mattson, et al., *Light Chain Composition of CSF Oligoclonal IgG Bands* . . . , J. NeuroImm., 3:63 (1982). Indirect immunoprecipitation is used to measure kappa chains, lambda chains and whole IgG. This procedure does not directly test for free kappa light chains, but instead indirectly tests for the free light chains by subtracting the amount of whole IgG from the sum of the quantities of kappa and lambda chains. Thus, the radioimmunoassay disclosed by Mattson is indirect, imprecise and, therefore, limiting as a diagnostic tool.

Accordingly, an object of this invention is to provide an improved radioimmunoassay for MS which operates by detecting the presence of free kappa light chains in CSF.

A further object of this invention is to provide an improved radioimmunoassay for the diagnosis of MS which provides quantitative results.

An advantage of hhis invention is its high level of sensitivity in distinguishing between normal patients and patients affected with MS.

A further advantage of this invention is that the radioimmunoassay enables a standardized range for values of free kappa light chains to be established.

Finally, a feature of this invention is that the radioimmunoassay provided herein has an improved ability to distinguish between patients with MS and other patients with CSF disorders.

Briefly described, a quantitative radioimmunoassay, as a diagnostic tool for the detection of MS, is disclosed which comprises the steps of isolating free kappa light chains from a source, isolating an antiserum specific for free kappa light chains from another source, radiolabeling a portion of said free kappa light chains, combining known amounts of said free kappa light chains, said antiserum and said radiolabeled free kappa light chains, allowing said combination sufficient time to react, precipitating said combination to form a precipitate and counting the radioactivity of said precipitate. These steps can be repeated with a plurality of different amounts of said free kappa light chains to produce a standard curve. While the standard curve is being generated, the above-described steps may be repeated in series using a test sample. Said test sample comprises cerebral spinal fluid isolated from a patient. The test sample is substituted for said free kappa light chains in said combination. Results from test samples may be compared with the standard curve to estimate the level of free kappa light chains in the test sample as an indication of the levels of free kappa light chains in said patient and therefore of multiple sclerosis.

Figure 2:
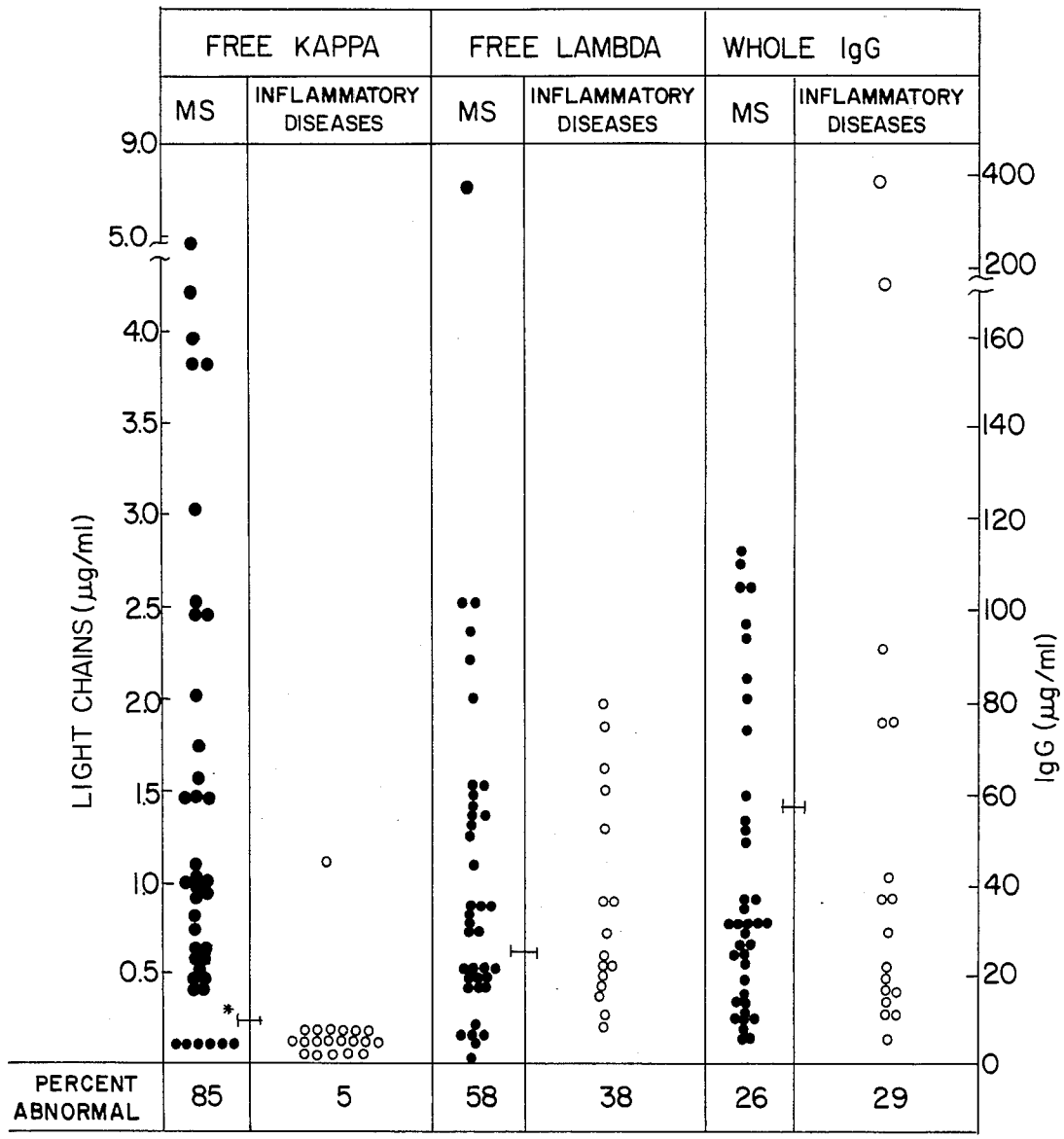

Other objects, advantages and features of this invention as well as the best known mode for the practice thereof will become apparent to those skilled in the art from a reading of the following detailed description with reference to the accompanying drawings in which:

FIG. 1 is plot of the percent of radioactive free kappa light chains bound as a function of the log concentration of unlabeled competitor, wherein the unlabeled competitor is free kappa light chains ( ), free lambda light chains ( ) or IgG ( ); and FIG. 2 is bar graph representing the amount of free kappa light chains, free lambda light chains and whole IgG, in $\mu$g/ml, found in patients with MS or with inflammatory diseases.

A quantitative radioimmunoassay (RIA) is used to quantitate free kappa light chains in CSF and serum. The first step is to isolate free kappa light chains from a source. In preparing a standard curve, a pool of 10 Bence-Jones kappa light chains, available from Tago, Inc., Burlingame, Calif., is used as the preferred source. Other sources include the blood or urine of humans wherein said light chains may be obtained by procedures known to those skilled in the art.

A portion of the kappa light chains isolated then are labeled with $^{125}$I by the chloramine T method to a specific activity of 15-25 Ci/gm. The next step is to isolate an antiserum specific for free kappa light chains from a source. The antiserum, available from Dakopatt,, Copehagen, Denmark, is used as the preferred source. Other sources include antibodies produced in animals immunized with pooled Bence-Jones kappa chains, wherein said antibodies are then extensively absorbed with whole IgG, leaving only specific antibodies that reacted with "hidden" determinants of kappa chains (i.e., the antibodies react with free kappa light chains but not whole IgG).

An optimal amount of said antiserum then is combined at 37° C. with 5 ng $^{125}$I-kappa in the presence of a plurality of amounts (e.g., serial dilutions) of unlabeled kappa light chains. In the preferred embodiment, the amounts of antiserum and radiolabeled free kappa light chains are 20 µl and 50 µl respectively. The volume of the free kappa light chains may range between 20 µl and 100 µl. The combination then is allowed a sufficient time to react. In the preferred embodiment, 1 hour is sufficient. The final volume in the assay is made up to 500 µl with a buffered salt solution.

Bound $^{125}$I kappa in said combination is precipitated from solution using insoluble staphyloccocal protein A (Pansorbin; available from Calbiochem, San Diego, Calif.). The precipitate is washed three times in phosphate buffered saline (PBS) before gamma counting. From this, a standard curve is developed. The sensitivity of the assay was 0.25 µg/ml, the within-assay coefficient of variation (CV) was 2.6%, and the between-assay CV was 9.2%.

In the preferred embodiment, while the standard curve is being developed, test samples, comprising CSF or serum isolated from a patient, are run in series. The test samples are substituted for the unlabeled kappa light chains in the combination. The volume of the test sample ranges from 20 to 100 µl. The results obtained from the test sample then are compared with the standard curve to estimate the amount of free kappa light chains in the test sample in order to determine if the patient has normal amounts or amounts indicative of a diagnosis of MS. Although the standard curve need not be generated in series with test samples, creating a standard curve along with test samples will reduce between experiment variation.

It is to be appreciated that a RIA for free lambda light chains also may be run similar to the free kappa light chain RIA with appropriate subttitutions of materials. Likewise, a RIA for whole IgG is well-known to those skilled in the art. Neither assay, however, provides the diagnostic detail present in this invention.

Referring to FIG. 1, since free kappa light chains in CSF and serum must be measured in the presence of excess whole IgG, it is important to test the specificity of the assay for free kappa light chains relative to whole IgG. The kappa antiserum immunoprecipitates free light chains but not whole IgG, as shown by Ouchterlony immunodiffusion. Purified human IgG, free kappa and lambda light chains were used as unlabeled competitors in the RIA. There was no cross-reactivity between kappa and lambda light chains in the free kappa chain assay. Whole IgG for these experiments was isolated from normal human serum by DEAE anion exchange chromatography followed by gel chromatography of Sephadex G-200 to remove contaminating free light chains. Displacement of $^{125}$I-kappa required a 4-log weight or a $1.65 \times 10^3$ molar excess of whole IgG. See FIG. 1. Thus, this assay is sufficiently specific to permit analysis of free kappa light chains in samples of whole CSF or serum without interference from whole IgG present in the samples.

In order to establish that the radioimmunassay would function quantitatively to detect MS, MS patients and control patients scheduled to undergo lumbar puncture for clinical indications were examined and their medical records were reviewed. In addition, samples were studied from 4 normal volunteers. Clinical diagnoses were made by an observer prior to analysis of the CSF using the method of Poser. See Poser, et al., *New Diagnostic Criteria for Multiple Sclerosis...*, Ann. Neurol., 13:227 (1983).

Forty-one patients met the Poser criteria for definite MS, 23 controls had noninflammatory conditions and 19 controls had inflammatory or infectious diseases of the nervous system. See Table 1. The noninflammatory control group, which included 4 normal individuals, was used to develop normative data for the RIA. The inflammatory disease control group included 9 patients with established viral or bacterial infections. Results from the MS patients were compared with this latter control group. Serum samples were studied from 24 of the patients with MS and from 12 control patients. Samples of CSF and serum were collected within 1 hour of the lumbar puncture and stored at −70° C. in 1 to 2 ml aliquots. Freeze-thaw cycles were avoided.

TABLE 1

PATIENTS INCLUDED IN STUDY

| PATIENT GROUP | DISEASE | NUMBER | |
|---|---|---|---|
| MULTIPLE SCLEROSIS | MS - Remitting | 16 | 41 |
| | MS - Progressive | 25 | |
| NONINFLAMMATORY DISEASES | Polyneuropathy | 2 | 23 |
| | Migraine | 2 | |
| | Cerebellar degenertion | 2 | |
| | Myelopathy (spondylosis) | 1 | |
| | Pituitary tumor | 1 | |
| | Spinal stenosis | 1 | |
| | Pseudodementia | 1 | |
| | Lumbosacral discs | 9 | |
| | Normal volunteers | 4 | |
| INFLAMMATORY & INFECTIOUS DISEASES | Guillaine-Barre syndrome | 2 | 19 |
| | CNS lupus | 3 | |
| | Inflammatory neuropathy | 2 | |
| | Transverse myelitis | 1 | |
| | Aseptic meningitis | 1 | |
| | Arachnoiditis | 1 | |
| | H. flu meningitis | 5 | |
| | Enterovirus meningitis | 4 | |

Data derived from the noninflammatory control group was used to generate normative data for the RIAs. See Table 2. The non-inflammatory control group was used for this purpose since it has been shown that normal individuals have lower CSF IgG concentrations than do patients with noninflammatory neurologic diseases. None of the 24 control patients had detectable free kappa light chains in CSF. Therefore, the lower limit of sensitivity, 0.25 µg/ml, was used as the upper limit of normal (UNL) for CSF kappa light chains. The mean concentration of free lambda light chains was 0.34 µg/ml; the upper limit of normal was 0.63 µg/ml. The mean concentration of IgG was 23 µg/ml; the upper limit of normal was 57 µg/ml.

TABLE 2

NORMATIVE DATA
Derived From Noninflammatory
Disease Controls

| | # | MEAN (ug/ml) | SD | ULN (ug/ml) |
|---|---|---|---|---|
| KAPPA CHAINS | 24 | <.25 | NA | <.25 |
| LAMBDA CHAINS | 21 | 0.34 | 0.15 | 0.63 |

TABLE 2-continued

NORMATIVE DATA
Derived From Noninflammatory
Disease Controls

|  | # | MEAN (ug/ml) | SD | ULN (ug/ml) |
|---|---|---|---|---|
| WHOLE IgG | 24 | 23 | 17 | 57 |

RIA results from the patients with MS were compared with the inflammatory controls. See FIG. 2. Thirty-two (85%) of 38 MS patients had detectable CSF free kappa light chains; the mean concentration in this group was 1.4 µg/ml (range 0.25–4.94 µg/ml). In contrast, only 1 of 19 inflammatory controls had detectable free kappa light chains. The difference between the findings in these two groups, statistically, was highly significant. In contrast to the levels of free kappa light chains, the concentration of IgG or free lambda light chains did not distinguish between the MS and inflammatory control groups. Additional relevant parameters in the patient groups are depicted in Table 3.

TABLE 3

MS VS CONTROL GROUPS
CSF Findings

|  | AGE | KAPPA CHAINS (ug/ml) | LAMBDA CHAINS (ug/ml) | IGG (ug/ml) | CSF PROTEIN (mg %) | CSF CELLS (/mm3) |
|---|---|---|---|---|---|---|
| MS | 37 | 1.40 | 1.12 | 44 | 42 | 14 |
| INFLAMMATORY CONTROLS | 23 | 0.06 | 0.85 | 62 | 101 | 5906 |
| NONINFLAM CONTROLS | 42 | 0 | 0.34 | 23 | 38 | 2 |

The correlations between assays was evaluated by linear regression analysis. The levels of free lambda light chains correlated poorly with IgG ($r=0.35$) or with free kappa light chains ($r=0.35$), but there was a better correlation between free kappa light chains and IgG in the MS patients ($r=0.81$). The concentration of free kappa light chains correlated poorly with the concentration of CSF albumin ($r=0.34$) or total protein, as determined by the method of Lowry, ($r=0.53$).

Patients with the remitting form of MS, and those with the progressive form had similar levels of free light chains and IgG. The concentration of free kappa light chains was slightly higher, and the concentration of free lambda light chains slightly lower in patients in the remitting group. This resulted in a significant difference in the kappa:lambda ratio in remitting (1.72) compared to progressive (1.02) MS (Student's Two-Tailed T Test; $p<0.05$). Patients with negative kappa assays had a lower concentration of total IgG (22 vs 80 µg/ml; Student's Two-Tailed T Test; $p<0.001$), a lower CSF cell count (3 vs 16; Student's Two-Tailed T Test; $p<0.05$), and a lower frequency of oligoclonal bands as determined by gel electrophoresis (0% vs 85%; Chi Square; $p<0.001$) than did MS patients with detectable free kappa light chains. There was no difference in the length of time from disease onset (96 vs 116 months, not significant), nor any evident relationship to clinical disease activity.

Although CSF free kappa light chain levels were signifcantly higher in MS patients than controls, no significant differences in serum levels were seen between groups (not shown). The mean concentration of free kappa light chains in MS patients was $2.85+/-0.95$ µg/ml (n=24) and $3.36+/-0.60$ µg/ml (n=12) in control patients (Student's Two-tailed T Test; p=0.1).

Free kappa light chains were quantitated in matched serum and CSF pairs from 8 patients with MS and 5 control patients. See Table 4. The concentration of free kappa light chains in CSF in the MS patients was $1.21+/-0.81$ µg/ml. In matched serum samples, the concentration of kappa chains was $2.96+/-0.81$ µg/ml. The mean CSF/serum ratio for free kappa light chains in the MS patients was 0.39, while in the controls the CSF serum ratio was 0.07.

In order to determine the degree of CSF concentration of free kappa light chains relative to other proteins, the CSF/serum ratio for free kappa light chains was compared with the CSF/serum ratio for reference proteins. For this purpose, the CSF/serum ratio for albumin and gamma globulins was calculated in the CSF/serum pairs from the MS patients. The mean CSF/serum ratio for albumin was 0.0071, and for gamma globulin 0.0052. This indicated that free kappa light chains were concentrated 71-fold in CSF relative to albumin, and 121-fold relative to gamma globulins. These results indicates that free kappa light chains were selectively increased in CSF compared with other proteins.

TABLE 4

CSF:SERUM RATIOS
Kappa chains, Albumin, Gamma Globulins

| KAPPA (ug/ml) | | CSF:SERUM RATIO | | | CONCENTRATION OF KAPPA RELATIVE TO: | |
|---|---|---|---|---|---|---|
| CSF | SERUM | KAPPA | ALBUMIN | GLOBULIN | ALBUMIN | GLOBULINS |
| 1.30 | 1.95 | 0.667 | 0.004 | 0.002 | 171 | 351 |
| 0.84 | 2.80 | 0.300 | 0.005 | 0.002 | 64 | 130 |
| 0.92 | 2.00 | 0.460 | 0.006 | 0.003 | 73 | 159 |
| 2.05 | 4.50 | 0.456 | 0.007 | 0.007 | 70 | 68 |
| 0.58 | 3.30 | 0.176 | 0.011 | 0.004 | 16 | 44 |
| 0.55 | 2.30 | 0.239 | 0.006 | 0.004 | 41 | 54 |
| 0.90 | 3.20 | 0.281 | 0.007 | 0.004 | 39 | 67 |
| 2.55 | 3.60 | 0.708 | 0.008 | 0.008 | 92 | 89 |
| 1.21 | 2.96 | 0.411 | 0.007 | 0.004 | 71 | 120 |

Variations and modifications of the above-described invention may suggest themselves to those skilled in the art. Accordingly, the above-description should not be taken in any limiting sense.

We claim:

1. In the diagnosis of multiple sclerosis by detecting components of the cerebrospinal fluid of a patient, the improvement which comprises directly determining by a quantitative immunoassay the quantity of free kappa light chains in the cerebrospinal fluid by combining the free kappa light chains in the fluid with antiserum specific thereto, and from the quantity determined diagnosing whether said patient has multiple Sclerosis.

2. A method for the detection of multiple sclerosis by a quantitative radioimmunoassay which comprises the steps of:

1-combining separately a plurality of different amounts of free kappa light chains with an antibody specific therefor and with radiolabeled free kappa light chains, 2-measuring the radioactivity present in said combinations, 3-combining cerebral spinal fluid of a patient with said antibody and said radiolabeled free kappa light chains, 4- measuring the radioactivity of the combination formed in step 3 and 5-comparing the radioactivity level of step 2 with that of step 4 to determine if said patient has multiple sclerosis.

3. A method for the detection of multiple sclerosis by a quantitative radioimmunoassay, which comprises the steps of:

1-isolating free kappa light chains from a source, 2-isolating an antiserum specific for free kappa light chains from another source, 3-radiolabeling a portion of said free kappa light chains, 4-combining an amount of said free kappa light chains with optimal amounts of said antiserum and said radiolabeled free kappa light chains, 5-allowing said combination sufficient time to react and form a precipitate, and 6-measuring the radioactivity of said precipitate;

7-repeating steps 4–6 with a plurality of different amounts of free kappa light chains to produce a standard curve;

8-repeating steps 4–6 with a test sample substituted for said free kappa light chains in step 4, wherein said test sample comprises cerebral spinal fluid isolated from a patient; and 9-comparing the result of step 8 with the standard curve set forth in step 7 as an indication of the quantity of free kappa light chains in said patient and determining from said quantity of free kappa light chains whether said patient has multiple sclerosis.

4. The method as set forth in claim 3 wherein said antiserum comprises an antiserum isolated from animals immunized with pooled Bence-Jones kappa light chains, and wherein said antiserum has been absorbed with whole immunoglobin G.

5. The method as set forth in claim 3 wherein said optimal amount of antiserum is 20 $\mu$l.

6. The method as set forth in claim 3 wherein said optimal amount of radiolabeled free kappa light chain is 50 $\mu$l.

7. The method as set forth in claim 3 wherein said amount of free kappa light chains or test sample is between 20 and 100 $\mu$l.

* * * * *